United States Patent
Chaudhary

(10) Patent No.: US 6,994,961 B1
(45) Date of Patent: Feb. 7, 2006

(54) GENE EXPRESSION IN ECTODERMAL DYSPLASIA

(75) Inventor: Preet M. Chaudhary, Dallas, TX (US)

(73) Assignee: Board of Regent, The University of Texas System, Austin, TX (US)

( * ) Notice: Subject to any disclaimer, the term of this patent is extended or adjusted under 35 U.S.C. 154(b) by 251 days.

(21) Appl. No.: 09/490,187

(22) Filed: Jan. 23, 2000

(51) Int. Cl.
*C12Q 1/68* (2006.01)
(52) U.S. Cl. ................................. 435/6; 435/4; 435/7.1
(58) Field of Classification Search .................... 435/4, 435/6, 7.1; 514/4, 22
See application file for complete search history.

(56) References Cited

OTHER PUBLICATIONS

Eby et al, TAJ, a Novel Member of the Tumor Necrosis Factor Receptor Family, Activates the c-Jun N-terminal Kinase Pathway and Mediates Caspase-independent Cell Death, May 2000, The Journal of Biological Chemistry, vol. 275, No. 20, pp. 15336-13542.*

* cited by examiner

*Primary Examiner*—Sean McGarry
(74) *Attorney, Agent, or Firm*—Richard Aron Osman

(57) ABSTRACT

The invention provides methods and compositions for diagnosing and treating ectodermal disorders, particularly ectodermal dysplasia syndromes such as Clouston syndrome, which are associated with misexpression of a TAJ gene. Methods detect the presence of or predisposition to an ectodermal disorder by (a) detecting the presence of a TAJ gene or gene product in a cell; and (b) correlating the presence of the TAJ gene or gene product with a presence of or predisposition to an ectodermal disorder. Other methods modulate the functional expression of a TAJ gene or gene product in a cell comprising the step(s) of contacting a cell with an agent which specifically binds and modulates the functional expression of a TAJ gene or gene product, wherein (a) the cell is an ectodermal cell; or (b) the cell is a germ cell which gives rise to progeny ectodermal cells and detecting the functional expression of the TAJ gene or gene product in the progeny cells.

3 Claims, No Drawings

SEQUENCE LISTING

<160> NUMBER OF SEQ ID NOS: 2

<210> SEQ ID NO 1
<211> LENGTH: 1489
<212> TYPE: DNA
<213> ORGANISM: human
<220> FEATURE:
<221> NAME/KEY: CDS
<222> LOCATION: (65)..(1333)

<400> SEQUENCE: 1

```
ggacctgcag cctcccaggt ggctgggaag aactctccaa caataaatac atttgataag        60 aaag atg gct tta aaa gtg cta cta gaa caa gag aaa acg ttt ttc act        109
     Met Ala Leu Lys Val Leu Leu Glu Gln Glu Lys Thr Phe Phe Thr
       1               5                  10                  15 ctt tta gta tta cta ggc tat ttg tca tgt aaa gtg act tgt gaa tca        157
Leu Leu Val Leu Leu Gly Tyr Leu Ser Cys Lys Val Thr Cys Glu Ser
                 20                  25                  30 gga gac tgt aga cag caa gaa ttc agg gat cgg tct gga aac tgt gtt        205
Gly Asp Cys Arg Gln Gln Glu Phe Arg Asp Arg Ser Gly Asn Cys Val
             35                  40                  45 ccc tgc aac cag tgt ggg cca ggc atg gag ttg tct aag gaa tgt ggc        253
Pro Cys Asn Gln Cys Gly Pro Gly Met Glu Leu Ser Lys Glu Cys Gly
         50                  55                  60 ttc ggc tat ggg gag gat gca cag tgt gtg gcg tgc cgg ctg cac agg        301
Phe Gly Tyr Gly Glu Asp Ala Gln Cys Val Ala Cys Arg Leu His Arg
     65                  70                  75 ttc aag gag gac tgg ggc ttc cag aaa tgc aag ccc tgt ctg gac tgc        349
Phe Lys Glu Asp Trp Gly Phe Gln Lys Cys Lys Pro Cys Leu Asp Cys
 80                  85                  90                  95 gca gtg gtg aac cgc ttt cag aag gca aat tgt tca gcc acc agt gat        397
Ala Val Val Asn Arg Phe Gln Lys Ala Asn Cys Ser Ala Thr Ser Asp
                100                 105                 110 gcc atc tgc ggg gac tgc ttg cca gga ttt tat agg aag acg aaa ctt        445
Ala Ile Cys Gly Asp Cys Leu Pro Gly Phe Tyr Arg Lys Thr Lys Leu
            115                 120                 125 gtc ggc ttt caa gac atg gag tgt gtg cct tgt gga gac cct cct cct        493
Val Gly Phe Gln Asp Met Glu Cys Val Pro Cys Gly Asp Pro Pro Pro
        130                 135                 140 cct tac gaa ccg cac tgt gcc agc aag gtc aac ctc gtg aag atc gcg        541
Pro Tyr Glu Pro His Cys Ala Ser Lys Val Asn Leu Val Lys Ile Ala
    145                 150                 155 tcc acg gcc tcc agc cca cgg gac acg gcg ctg gct gcc gtt atc tgc        589
Ser Thr Ala Ser Ser Pro Arg Asp Thr Ala Leu Ala Ala Val Ile Cys
160                 165                 170                 175 agc gct ctg gcc acc gtc ctg ctg gcc ctg ctc atc ctc tgt gtc atc        637
Ser Ala Leu Ala Thr Val Leu Leu Ala Leu Leu Ile Leu Cys Val Ile
                180                 185                 190 tat tgt aag aga cag ttt atg gaa aag aaa ccc agc tgg tct ctg cgg        685
Tyr Cys Lys Arg Gln Phe Met Glu Lys Lys Pro Ser Trp Ser Leu Arg
            195                 200                 205 tca cag gac att cag tac aac gag act gag ctg tcg tgt ttt gac aga        733
Ser Gln Asp Ile Gln Tyr Asn Glu Thr Glu Leu Ser Cys Phe Asp Arg
        210                 215                 220 cct cag ctc cac gaa tat gcc cac aga gcc tgc tgc cag tgc cgc cgt        781
Pro Gln Leu His Glu Tyr Ala His Arg Ala Cys Cys Gln Cys Arg Arg
    225                 230                 235
```

-continued

| | |
|---|---|
| gac tca gtg cag acc tgc ggg ccg gtg cgc ttg ctc cca tcc atg tgc<br>Asp Ser Val Gln Thr Cys Gly Pro Val Arg Leu Leu Pro Ser Met Cys<br>240                              245                            250                            255 | 829 |
| tgt gag gag gcc tgc agc ccc aac ccg gcg act ctt ggt tgt ggg gtg<br>Cys Glu Glu Ala Cys Ser Pro Asn Pro Ala Thr Leu Gly Cys Gly Val<br>                              260                            265                            270 | 877 |
| cat tct gca gcc agt ctt cag gca aga aac gca ggc cca gcc ggg gag<br>His Ser Ala Ala Ser Leu Gln Ala Arg Asn Ala Gly Pro Ala Gly Glu<br>                      275                            280                            285 | 925 |
| atg gtg ccg act ttc ttc gga tcc ctc acg cag tcc atc tgt ggc gag<br>Met Val Pro Thr Phe Phe Gly Ser Leu Thr Gln Ser Ile Cys Gly Glu<br>                  290                            295                            300 | 973 |
| ttt tca gat gcc tgg cct ctg atg cag aat ccc atg ggt ggt gac aac<br>Phe Ser Asp Ala Trp Pro Leu Met Gln Asn Pro Met Gly Gly Asp Asn<br>305                              310                            315 | 1021 |
| atc tct ttt tgt gac tct tat cct gaa ctc act gga gaa gac att cat<br>Ile Ser Phe Cys Asp Ser Tyr Pro Glu Leu Thr Gly Glu Asp Ile His<br>320                              325                            330                            335 | 1069 |
| tct ctc aat cca gaa ctt gaa agc tca acg tct ttg gat tca aat agc<br>Ser Leu Asn Pro Glu Leu Glu Ser Ser Thr Ser Leu Asp Ser Asn Ser<br>                              340                            345                            350 | 1117 |
| agt caa gat ttg gtt ggt ggg gct gtt cca gtc cag tct cat tct gaa<br>Ser Gln Asp Leu Val Gly Gly Ala Val Pro Val Gln Ser His Ser Glu<br>                  355                            360                            365 | 1165 |
| aac ttt aca gca gct act gat tta tct aga tat aac aac aca ctg gta<br>Asn Phe Thr Ala Ala Thr Asp Leu Ser Arg Tyr Asn Asn Thr Leu Val<br>                  370                            375                            380 | 1213 |
| gaa tca gca tca act cag gat gca cta act atg aga agc cag cta gat<br>Glu Ser Ala Ser Thr Gln Asp Ala Leu Thr Met Arg Ser Gln Leu Asp<br>385                              390                            395 | 1261 |
| cag gag agt ggc gct gtc atc cac cca gcc act cag acg tcc ctc cag<br>Gln Glu Ser Gly Ala Val Ile His Pro Ala Thr Gln Thr Ser Leu Gln<br>400                              405                            410                            415 | 1309 |
| gta agg cag cga ctg ggt tcc ctg tgaacacagc actgacttac agtagatcag<br>Val Arg Gln Arg Leu Gly Ser Leu<br>                  420 | 1363 |
| aactctgttc ccagcataag atttggggga acctggatga gtttttttt ttgcatcttt | 1423 |
| aataatttct tatatgttgt agagtatgtt ttaaaataaa tttcaagtat ttttttaaaa | 1483 |
| aacttt | 1489 |

<210> SEQ ID NO 2
<211> LENGTH: 423
<212> TYPE: PRT
<213> ORGANISM: human

<400> SEQUENCE: 2

Met Ala Leu Lys Val Leu Leu Glu Gln Glu Lys Thr Phe Phe Thr Leu
1               5                   10                  15

Leu Val Leu Leu Gly Tyr Leu Ser Cys Lys Val Thr Cys Glu Ser Gly
            20                  25                  30

Asp Cys Arg Gln Gln Glu Phe Arg Asp Arg Ser Gly Asn Cys Val Pro
        35                  40                  45

Cys Asn Gln Cys Gly Pro Gly Met Glu Leu Ser Lys Glu Cys Gly Phe
    50                  55                  60

Gly Tyr Gly Glu Asp Ala Gln Cys Val Ala Cys Arg Leu His Arg Phe
65                  70                  75                  80

-continued

```
Lys Glu Asp Trp Gly Phe Gln Lys Cys Lys Pro Cys Leu Asp Cys Ala
                    85                  90                  95
Val Val Asn Arg Phe Gln Lys Ala Asn Cys Ser Ala Thr Ser Asp Ala
                100                 105                 110
Ile Cys Gly Asp Cys Leu Pro Gly Phe Tyr Arg Lys Thr Lys Leu Val
                115                 120                 125
Gly Phe Gln Asp Met Glu Cys Val Pro Cys Gly Asp Pro Pro Pro
            130                 135                 140
Tyr Glu Pro His Cys Ala Ser Lys Val Asn Leu Val Lys Ile Ala Ser
145                 150                 155                 160
Thr Ala Ser Ser Pro Arg Asp Thr Ala Leu Ala Ala Val Ile Cys Ser
                165                 170                 175
Ala Leu Ala Thr Val Leu Leu Ala Leu Leu Ile Leu Cys Val Ile Tyr
                180                 185                 190
Cys Lys Arg Gln Phe Met Glu Lys Lys Pro Ser Trp Ser Leu Arg Ser
                195                 200                 205
Gln Asp Ile Gln Tyr Asn Glu Thr Glu Leu Ser Cys Phe Asp Arg Pro
                210                 215                 220
Gln Leu His Glu Tyr Ala His Arg Ala Cys Cys Gln Cys Arg Arg Asp
225                 230                 235                 240
Ser Val Gln Thr Cys Gly Pro Val Arg Leu Leu Pro Ser Met Cys Cys
                245                 250                 255
Glu Glu Ala Cys Ser Pro Asn Pro Ala Thr Leu Gly Cys Gly Val His
                260                 265                 270
Ser Ala Ala Ser Leu Gln Ala Arg Asn Ala Gly Pro Ala Gly Glu Met
                275                 280                 285
Val Pro Thr Phe Phe Gly Ser Leu Thr Gln Ser Ile Cys Gly Glu Phe
                290                 295                 300
Ser Asp Ala Trp Pro Leu Met Gln Asn Pro Met Gly Gly Asp Asn Ile
305                 310                 315                 320
Ser Phe Cys Asp Ser Tyr Pro Glu Leu Thr Gly Glu Asp Ile His Ser
                325                 330                 335
Leu Asn Pro Glu Leu Glu Ser Ser Thr Ser Leu Asp Ser Asn Ser Ser
                340                 345                 350
Gln Asp Leu Val Gly Gly Ala Val Pro Val Gln Ser His Ser Glu Asn
                355                 360                 365
Phe Thr Ala Ala Thr Asp Leu Ser Arg Tyr Asn Asn Thr Leu Val Glu
                370                 375                 380
Ser Ala Ser Thr Gln Asp Ala Leu Thr Met Arg Ser Gln Leu Asp Gln
385                 390                 395                 400
Glu Ser Gly Ala Val Ile His Pro Ala Thr Gln Thr Ser Leu Gln Val
                405                 410                 415
Arg Gln Arg Leu Gly Ser Leu
                420
```

GENE EXPRESSION IN ECTODERMAL DYSPLASIA

FIELD OF THE INVENTION

The field of the invention is TAJ gene expression in ectodermal disorders.

BACKGROUND

The ectodermal dysplasia syndromes are a group of genetic disorders which are identified by the absent or deficient function of derivatives of ectoderm (e.g. skin, nail, sweat glands or teeth). At least 150 different syndromes have been identified and it is estimated that the incidence of these disorders may be as high as 7 per 10,000 births. Two major subgroups of ectodermal dysplasias are hypohidrotic ectodermal dysplasia (HED) and hidrotic ectodermal dysplasia or Clouston syndrome (Ellis et al., 1980, Clin Exp Dermatol 5, 295–304; Pinheiro et al., 1994, Am J Med Genet 53, 153–162; Kere et al., 1997, U.S. Pat. No. 5,700,926).

Mutations in the human homolog of mouse dl have recently been reported to cause autosomal recessive and dominant hypohidrotic ectodermal dysplasia (Monreal, et al. 1999 Nature Gen 22, 366–369; Headon et al. 1999 Nature Gen 22, 370–374. We previously isolated a new member of the TNFR family, designated TAJ (originally, APO4, Chaudhary, 1999, WO9911791) and characterized its expression in embryonic and prostate tissue. Here we disclose that TAJ may be exploited for post and pre-natal diagnosis and treatment of ectodermal disorders such as Clouston syndrome.

SUMMARY OF THE INVENTION

The invention provides methods and compositions for diagnosing and treating ectodermal disorders associated with misexpression of a TAJ gene. In one embodiment, the invention provides methods of detecting the presence of or predisposition to an ectodermal disorder comprising the steps of (a) detecting the presence of a TAJ gene or gene product in a cell; and (b) correlating the presence of the TAJ gene or gene product with a presence of or predisposition to an ectodermal disorder. The detection may be direct, indirect or inferential and at the level of the TAJ gene, transcript, protein or any intermediate processing stage. In particular embodiments, the detecting step is performed inferentially by determining a diagnostic sequence of the TAJ gene or gene product in the individual; the TAJ gene or gene product is a variant correlated with the presence of or predisposition to an ectodermal disorder; the ectodermal disorder is an ectodermal dysplasia syndrome, such as Clouston syndrome.

In another embodiment, the invention provides a method for modulating the functional expression of a TAJ gene or gene product in a cell comprising the step(s) of contacting a cell with an agent which specifically binds and modulates the functional expression of a TAJ gene or gene product, wherein (a) the cell is an ectodermal cell; or (b) the cell is a pluripotent cell which is capable of giving rise to progeny ectodermal cells and detecting the functional expression of the TAJ gene or gene product in the progeny cells. In particular embodiments, the cell is in situ or ex situ, the contacting step reduces or increases the functional expression of the TAJ gene or gene product, the agent is an antibody or intrabody which specifically binds a TAJ protein; the agent is an agonist or antagonist of a TAJ protein; the agent is an antisense oligonucleotide which specifically binds a TAJ gene transcript; the agent is an oligonucleotide which specifically binds a TAJ gene, etc. In more particular embodiments, the agent is an oligonucleotide which specifically binds a TAJ gene, whereby the gene is changed to a different TAJ gene, particularly whereby the gene is changed from a TAJ gene correlated with a presence of or predisposition to an ectodermal disorder to a different TAJ gene not so correlated, particularly wherein the ectodermal disorder is an ectodermal dysplasia syndrome, such as Clouston syndrome.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands, complements and reverse complements, as well as alternative backbones described herein.

The invention provides methods and compositions for diagnosing and treating an ectodermal disorder associated with misexpression of a TAJ gene. Ectodermal disorders manifest as the presence of or predisposition to disease in ectodermal cells or cells of ectodermal origin and include cells of or giving rise to skin, nails, teeth, hair follicles, sweat glands, etc. Exemplary ectodermal disorders include ectodermal dysplasia syndromes, such as Clouston syndrome.

The subject disorders may arise, inter alia, from temporal (e.g. at undesirable time), developmental (e.g. in undesirable cell type or developmental stage), quantitative (e.g. over- or under-expression) or qualitative (e.g. structural) TAJ misexpression. A wide variety of causalities may effect such misexpression, including genetic lesions or mutations to the TAJ gene itself or direct or indirect TAJ gene regulatory sequences, the misexpression of genes or gene products which in turn regulate TAJ gene expression or TAJ function, etc. Table 1 provides exemplary TAJ gene lesions shown to be associated with autosomal dominant or recessive ectodermal dysplasia, in hetero- or homozygotic mutants, respectively.

TABLE 1

Exemplary TAJ gene lesions shown to be associated with an ectodermal dysplasia. Nucleotide and amino acid positions are relative to wild-type, full-length human TAJ cDNA and protein sequences, SEQ ID NO:1 and 2, respectively.

| TAJ Mutant | Genetic Lesion | Translation Product | TAJ Structural Defect |
|---|---|---|---|
| hTm106 | C deletion at 384 | Ser to Stop at 107 | Truncation at residue 106 |
| hTm134 | T to A at 459 | Cys to Stop at 135 | Truncation at residue 134 |
| hTm174 | C deletion at 589 | Cys to Stop at 175 | Truncation at residue 174 |
| hTm191 | T to A at 639 | Tyr to Stop at 192 | Truncation at residue 191 |
| hTm212 | C to A at 703 | Tyr to Stop at 213 | Truncation at residue 212 |
| hTm219 | T to A at 724 | Cys to Stop at 220 | Truncation at residue 219 |
| hTm238 | CC deletion at 762 | Ala to Val at 233 | Truncation at residue 238 |
| hTm244 | C to A at 799 | Cys to Stop at 245 | Truncation at residue 244 |
| hTm268 | T to A at 871 | Cys to Stop at 269 | Truncation at residue 268 |
| hTm277 | C to T at 896 | Arg to Stop at 278 | Truncation at residue 277 |

TABLE 1-continued

Exemplary TAJ gene lesions shown to be associated with an ectodermal dysplasia. Nucleotide and amino acid positions are relative to wild-type, full-length human TAJ cDNA and protein sequences, SEQ ID NO:1 and 2, respectively.

| TAJ Mutant | Genetic Lesion | Translation Product | TAJ Structural Defect |
| --- | --- | --- | --- |
| hTm279 | A to T at 902 | Arg to Stop at 280 | Truncation at residue 279 |
| hTm286 | G to T at 923 | Glu to Stop at 287 | Truncation at residue 286 |
| hTm293 | G to T at 944 | Gly to Stop at 294 | Truncation at residue 293 |

In one embodiment, the invention provides methods of detecting the presence of or predisposition to an ectodermal disorder comprising the steps of (a) detecting the presence of a TAJ gene or gene product in a cell; and (b) correlating the presence of the TAJ gene or gene product with a presence of or predisposition to an ectodermal disorder.

A wide variety of methods may be used to detect the TAJ gene or gene product. The detection may be by any convenient method and may be direct, indirect or inferential and at the level of the TAJ gene, transcript, protein or any intermediate processing stage. Direct detection of the target TAJ molecule is typically effected with sequencing reagents, sensors, such as mass or emission or absorption spectrometers, or specific binding molecules such as, in the case of a TAJ protein target, specific antibodies or T-cell antigen receptors, extracellular ligands, agonists or antagonists, intracellular binding agents such as TRAF 1, 2, 3 and 5 or such agents identified with assays such as one-, two- and three-hybrid screens, non-natural intracellular binding agents identified in binding assay screens of chemical libraries such as described below, etc. In the case of a TAJ polynucleotide target, specific binding agents include allele-specific hybridization probes, amplification primers, etc. In a preferred embodiment, probes are immobilized in high density microarrays. A wide variety of materials and methods are known in the art for arraying polynucleotides at discrete elements of substrates such as glass, silicon, plastics, nylon membranes, etc., including contact deposition, e.g. U.S. Pat. Nos. 5,807,522; 5,770,151, DeRisi J L, et al. Curr Opin Oncol 1999 Jan.; 11 (1):76–9, etc.; photolithography-based methods, e.g. U.S. Pat. Nos. 5,861,242; 5,858, 659; 5,856,174; 5,856,101; 5,837,832, Lipshutz R J, et al. Nat Genet 1999 Jan.; 21(1 Suppl):20–4, etc.; inkjet dispensing technologies, e.g. Lemmo A V, et al., Curr Opin Biotechnol 1998 Dec.; 9(6):615–7; flow path-based methods, e.g. U.S. Pat. No. 5,384,261; dip-pen nanolithography-based methods, e.g. Piner, et al., Science Jan. 29 1999:661–663, etc.; etc. Table 2 provides exemplary allele-specific TAJ antibodies and hybridization probes.

TABLE 2

Exemplary allele-specific TAJ antibodies and hybridization probes. Nucleotide and amino acid positions are relative to wild type, full-length human TAJ cDNA and protein sequences, SEQ ID NO:1 and 2, respectively. Designated antibodies are murine monoclonal (m) or rabbit affinity purified (r): allele-specific oligonucleotide (ASO) probes comprise the complement of the corresponding genetic lesion.

| TAJ Mutant | Allele-specific antibody | Specific Binding | Allele specific oligonucleotide | Specific Hybridization |
| --- | --- | --- | --- | --- |
| hTm106 | Ab106m | +++ | ASO106 (SEQ ID NO:1, nucleotides 372–396) | +++ |

TABLE 2-continued

Exemplary allele-specific TAJ antibodies and hybridization probes. Nucleotide and amino acid positions are relative to wild type, full-length human TAJ cDNA and protein sequences, SEQ ID NO:1 and 2, respectively. Designated antibodies are murine monoclonal (m) or rabbit affinity purified (r): allele-specific oligonucleotide (ASO) probes comprise the complement of the corresponding genetic lesion.

| TAJ Mutant | Allele-specific antibody | Specific Binding | Allele specific oligonucleotide | Specific Hybridization |
| --- | --- | --- | --- | --- |
| hTm134 | Ab134m | +++ | ASO134 (SEQ ID NO:1, nucleotides 447–471) | +++ |
| hTm174 | Ab174m | +++ | ASO174 (SEQ ID NO:1, nucleotides 577–601) | +++ |
| hTm191 | Ab191m | +++ | ASO191 (SEQ ID NO:1, nucleotides 627–651) | +++ |
| hTm212 | Ab212m | +++ | ASO212 (SEQ ID NO:1, nucleotides 691–715) | +++ |
| hTm219 | Ab219m | +++ | ASO219 (SEQ ID NO:1, nucleotides 712–736) | +++ |
| hTm238 | Ab238r | +++ | ASO238 (SEQ ID NO:1, nucleotides 750–774) | +++ |
| hTm244 | Ab244r | +++ | ASO244 (SEQ ID NO: 1, nucleotides 787–811) | +++ |
| hTm268 | Ab268m | +++ | ASO268 (SEQ ID NO:1, nucleotides 859–883) | +++ |
| hTm277 | Ab277m | +++ | ASO277 (SEQ ID NO:1, nucleotides 884–908) | +++ |
| hTm279 | Ab279m | +++ | ASO279 (SEQ ID NO:1, nucleotides 890–914) | +++ |
| hTm286 | Ab286r | +++ | ASO286 (SEQ ID NO:1, nucleotides 911–935) | +++ |
| hTm293 | Ab293r | +++ | ASO293 (SEQ ID NO:1, nucleotides 932–956) | +++ |

Indirect detection is typically effected by detecting a specific function of the target molecule, such as signal transduction (see, e.g. WO9911791 and Example II, below, for cell-based TAJ function assays) and inferential detection is typically effected by detecting a diagnostic sequence of the target molecule in a genomic or proteomic database representation of the cell. A diagnostic sequence comprises sufficient sequence information to correlate the corresponding TAJ gene or gene product with, or characterize the corresponding TAJ gene or gene product as a variant correlated with, the presence or predisposition to an ectodermal disorder. Hence, where sufficient genomic or proteomic information of the cell is known a priori, detection may be performed entirely in silico using a computer based algorithm, such as BLAST (e.g. Build sol2.5-x86 01:40:37 05 Feb. 1998, Copyright (C)1997 Warren R. Gish, using default parameters, Altschul et al., Methods in Enzymology, 215: 403–410 (1997)).

The correlating step involves determining whether the detected TAJ gene or gene product is associated with the presence of or predisposition to an ectodermal disorder. Large-scale TAJ genotypings predefine many correlates; hence in many instances the correlation step may be effected by simply identifying the detected TAJ gene or gene product as a known variant or allele and cross-referencing the predetermined clinical correlate. Such correlations are readily implemented by computer-based algorithms. In addition, known TAJ function and TAJ structure-activity relationships permit correlates to be inferred for many novel alleles and variants. For example, mutations effecting truncations proximate to residue 286 are known to be functionally inactive in the JNK activation assay (below) and associated with the presence of or predisposition to an ectodermal disorder. Correlates for other alleles or variants not predictable from known variants are readily inferred empirically from in vitro functional assays and/or determined empirically by conventional disease-genetic linkage analysis.

In another embodiment, the invention provides a method for modulating (i.e. increasing or, preferably, decreasing) the functional expression of a TAJ gene or gene product in a cell. Functional expression manifests as TAJ activity in the cell and hence, may be modulated at the level of TAJ transcription, translation, processing, location, protein function, etc. One aspect of this embodiment comprises the step of contacting an ectodermal cell with an agent which specifically binds and modulates the functional expression of a TAJ gene or gene product and, optionally detecting the functional expression of the TAJ gene or gene product in the progeny cells. Another aspect of this embodiment comprises the steps of (a) contacting an ectodermal pluripotent cell (i.e. a cell which gives rise or can be induced to give rise to progeny ectodermal cells, and including germ cells like sperm and egg cells, zygotes, unipotential or multipotential stem cells, etc.) with an agent which specifically binds and modulates the functional expression of a TAJ gene or gene product and (b) detecting the functional expression of the TAJ gene or gene product in the progeny cells.

A wide variety of modulating agents may be used. For example, where the target is a TAJ protein, agents include TAJ-specific binding agents such as antibodies and intrabodies, dominant-negative TAJ mutants, extracellular TAJ ligands, agonists or antagonists, intracellular binding agents, and particularly non-natural binding agents identified in in vitro screens of chemical libraries such as described below, etc. Where the target is a TAJ polynucleotide such as a gene or transcript, the modulators typically comprise sequence-specific complements such as antisense oligonucleotides, replacement vectors, RNA-DNA oligonucleotides, etc. Table 3 provides a number of exemplary agents shown to allele-specifically modulate functional expression of a TAJ gene or gene product. Detailed exemplification of several of these applications is provided in the Examples below.

TABLE 3

Exemplary agents shown to allele-specifically modulate functional expression of a TAJ gene or gene product (RDO, RNA-DNA oligonucleotide; TS, TAJ targeting component of RDO; IP, immunogenic peptide; AO, antisense oligonucleotide; RC, reverse complement; i.d., intradermal injection).

| Agent | Target Allele | Target Cell | Delivery | Modulation |
|---|---|---|---|---|
| hTm106RDO (TS, SEQ ID NO:1, nucleotides 372–396) | hTm106 | keratinocytes | topical, Cytofectin | +++ |
| hTm238RDO (TS, SEQ ID NO:1, nucleotides 750–774) | hTm238 | keratinocytes | topical, Cytofectin | +++ |
| hTm286RDO (TS, SEQ ID NO:1, nucleotides 911–935) | hTm286 | keratinocytes | topical, Cytofectin | +++ |
| hTm106RDO (TS, SEQ ID NO:1, nucleotides 372–396) | hTm106 | basal epidermal | topical, Cytofectin | +++ |
| hTm238RDO (TS, SEQ ID NO:1, nucleotides 750–774) | hTm238 | basal epidermal | topical, Cytofectin | +++ |
| hTm286RDO (TS, SEQ ID NO:1, nucleotides 911–935) | hTm286 | basal epidermal | topical, Cytofectin | +++ |
| Intrabody, IP106 (SEQ ID NO:2, residues 103–110) | hTm106 | basal epidermal | expression vector, i.d. | +++ |
| Intrabody, IP238 (SEQ ID NO:2, residues 234–243) | hTm238 | basal epidermal | expression vector, i.d. | +++ |
| Intrabody, IP286 (SEQ ID NO:2, residues 283–295) | hTm286 | basal epidermal | expression vector, i.d. | +++ |
| AO106 (SEQ ID NO:1, nucleotides 272–396, RC) | hTm106 | keratinocytes | i.d. | +++ |
| AO238 (SEQ ID NO:1, nucleotides 750–774, RC) | hTm238 | keratinocytes | i.d. | +++ |
| AO286 (SEQ ID NO:1, nucleotides 911–935, RC) | hTm286 | keratinocytes | i.d. | +++ |

The method of agent delivery depends on the nature of the modulator and target cell, which may be in situ (resident within the host individual) or ex situ. A wide variety of technologies for delivering therapeutic agents to epithelial cells, particularly skin are well known in the art, e.g. Somani et al., J Cutan Med Surg 1999 Jul; 3 (5):249–59; Proc Assoc Am Physicians 1999 May–Jun.; 111 (3)—whole issue; Sawamura et al. Gene Ther 1999 Oct.; 6 (10):1785–1787; and Van Steensel et al., Proc Soc Exp Biol Med 2000 Jan.; 223 (1):1–7, for a review of genetic delivery to hair follicles. In a particular embodiment, the agent is an oligonucleotide which specifically binds a TAJ gene, whereby the gene is changed to a different TAJ gene, particularly whereby the gene is changed from a TAJ gene correlated with a presence of or predisposition to an ectodermal disorder to a different TAJ gene not so correlated (see Examples, below).

EXAMPLES

I. Characterization of TAJ Expression, Correlation with Epithelial Disorders and Animal Model.

We sought to further characterize the expression of TAJ during embryogenesis, using in-situ hybridization. Major expression of TAJ in the 11.5 day embryo was detected on the ventral surface of the mandibular component of first branchial arch. More widespread expression of TAJ was seen in day 15.5 embryo with strong expression detected in the basal epithelium of skin and hair follicles. Regional variation in skin expression of TAJ was detected as well, with high level expression in the limbs, tail and head and lower expression on the trunk. Expression of TAJ was also seen in the meninges, thaliamus, ossification centers in left mandible and maxilla, tracheal rings, esophagus and adrenal glands.

The chromosomal location of hTAJ was mapped using the TNG radiation hybrid panel. Linkage was found to the markers SHGC-130802 and SHGC-2183 located on the chromosome 13 with LOD scores of 11.4 and 5.27, respectively. SHGC-2183 has been linked to a marker present in the 13q11.4 region, the locus of the gene for Clouston syndrome (Stevens et al., 1999, Br J Dermatol 140, 963–964; Taylor et al., 1997, J Invest Dermatol 11, 83–85).

Animal model of hidrotic ectodermal dysplasia or Clouston syndrome. Murine TAJ knock-outs are obtained by targeted disruption of mTAJ using homologous recombination in ES cells. Briefly, a genomic clone containing 10–15 kb fragment of mTAJ is obtained by PCR screening of a P1 mouse ES cell library (strain 129SV) (Genome Systems Inc) using mTAJ-specific primers. The PI insert is restriction mapped and a neomycin resistance expression cassette inserted to disrupt the 5' end of mTAJ at the beginning of the ligand-binding domain. The short arm of the construct is flanked by two copies of the HSV-TK gene expression cassette which allows for negative selection of non-homologous recombinants. The linearized targeting vector is electroporated into ES cells and doubly resistant homologous recombinants selected by southern analysis. The ES cells are introduced into blastocysts and reimplanted into the uteri of pseudopregnant foster mice. Two to three corrected targeted ES cell lines are used to generate chimeras. Chimeric mice are identified by coat color and germ-line transmission tested by southern analysis of tail DNA. Heterozygote mice are examined for any gross abnormalities and fertility. Heterozygotes are maintained in a breeding colony and intercrossed to generate homozygous offsprings. Litters obtained from the mating of heterozygous animals are genotyped to determine the proportion of TAJ-null offspring and their phenotype characterized.

II. TAJ Activates the JNK Pathway.

The ability of TAJ proteins to activate the JNK pathway upon transient overexpression in 293EBNA cells was tested using a luciferase-based c-Jun transcriptional assay. In this assay, luciferase expression is driven by JNK-mediated phosphorylation of the activation domain of the transcription factor c-Jun that is fused to the GAL4 DNA-binding domain. Functional TAJ proteins could strongly activate the JNK pathway in these cells which was comparable in magnitude to that observed with CD40. The ability of TAJ protein to activate the JNK pathway was also confirmed by a "pull-down" kinase assay kit (New England Biolabs) based on in vitro phosphorylation of GST-cJun, according to the manufacturer's specifications.

For the cJun transcriptional activation assay, 293 EBNA cells ($1.2 \times 10^5$) were plated in each well of 24-well plates. The next day, the cells were transfected in duplicate with empty expression vector or expression vector encoding TAJ or CD40 (500 ng) along with a fusion-transactivator plasmid containing the yeast GAL4 DNA-binding domain fused to transcription factor c-Jun (pFA-cJun) (50 ng), a reporter plasmid encoding the luciferase gene downstream of the GAL4 Upstream Activating sequence (pFR-luc) (500 ng), as well as a RSV/LacZ (beta-galactosidase) reporter construct (75 ng). All plasmids were purchased from Statagene. Transfection was performed using calcium phosphate coprecipitation method. Forty hours later cell extracts were prepared using the Luciferase Cell Culture Lysis Reagent (Promega, Madison, Wis.) and luciferase assays performed using 20 ul of cell extract. The cell lysate was diluted 1 to 20 with Phosphate Buffered Saline (pH=7.4) and used for the measurement of β-galactosidase activity (Molecular Cloning, A Laboratory Manual, Sambrook, et al. Cold Spring Harbor Laboratory). Luciferase activity was normalized relative to the β-galactosidase activity to control for the difference in the transfection efficiency.

III. Protocol for High Throughput TAJ Polypeptide-TRAF Binding Interference Assay.

A. Reagents:
Neutralite Avidin: 20 $\mu$g/ml in PBS.
Blocking buffer: 5% BSA, 0.5% Tween 20 in PBS; 1 hour at room temperature.
Assay Buffer: 100 mM KCl, 20 mM HEPES pH 7.6, 1 mM $MgCl_2$, 1% glycerol, 0.5% NP-40, 50 mM b-mercaptoethanol, 1 mg/ml BSA, cocktail of protease inhibitors.
$^{33}$P polypeptide 10x stock: $10^{-8}$–$10^{-6}$M "cold" TAJ intracellular domain (SEQ ID NO:2, residues 196–423) supplemented with 200,000–250,000 cpm of labeled TAH polypeptide (Beckman counter). Place in the 4° C. microfridge during screening.
Protease inhibitor cocktail (1000×): 10 mg Trypsin Inhibitor (BMB # 109894), 10 mg Aprotinin (BMB # 236624), 25 mg Benzamidine (Sigma # B-6506), 25 mg Leupeptin (BMB # 1017128), 10 mg APMSF (BMB # 917575), and 2 mM $NaVO_3$ (Sigma # S-6508) in 10 ml of PBS.
TRAF1: $10^{-7}$–$10^{-5}$ M biotinylated TRAF1 in PBS.

B. Preparation of Assay Plates:
Coat with 120 $\mu$l of stock N-Avidin per well overnight at 4° C.
Wash 2 times with 200 $\mu$l PBS.
Block with 150 $\mu$l of blocking buffer.
Wash 2 times with 200 $\mu$l PBS.

C. Assay:
Add 40 $\mu$l assay buffer/well.
Add 10 $\mu$l compound or extract.
Add 10 $\mu$L $^{33}$P-TAJ polypeptide (20–25,000 cpm/0.1–10 pmoles/well=$10^{-9}$–$10^{-7}$ M final conc).
Shake at 25° C. for 15 minutes.
Incubate additional 45 minutes at 25° C.
Add 40 $\mu$M biotinylated TRAF I (0.1–10 pmoles/40 ul in assay buffer)
Incubate 1 hour at room temperature.
Stop the reaction by washing 4 times with 200 $\mu$M PBS.
Add 150 $\mu$M scintillation cocktail.
Count in Topcount.

D. Controls for all Assays (Located on Each Plate):
a. Non-specific binding
b. Soluble (non-biotinylated TRAF1) at 80% inhibition IV. Genomic Diagnosis of Suspected Clouston's Syndrome.

Blood samples are taken from a patient with a suspected diagnosis of Clouston syndrome, and his parents, under approved institutional protocols for human subjects. The patient's father has a known history of Clouston syndrome caused by a GGA to TGA mutation at nucleotide position 944 of the TAJ cDNA which results in the production of a truncated protein of 293 amino acid. This mutation also results in the removal of a BamHI site present at that location. Genomic DNA is isolated with DNAzol (Molecular Research Center, Cincinnati, Ohio) from the blood samples and amplified by PCR to generate a TAJ gene fragment (forward primer: nucleotides 903–921 of SEQ ID NO: 1; reverse primer: reverse complement of nucleotides 1201–1220 of SEQ ID NO: 1). The purified PCR products are digested with BamHI restriction enzyme, and reaction products analyzed by 12% PAGE. Both the patient's and the father's sample show the presence of a mutant allele as demonstrated by the presence of an uncut PCR fragment of approximately 317 base pairs. A normal wild-type allele is also seen in the above samples, as demonstrated by the presence of two smaller fragments of approximately 41 and 276 base pairs, respectively. In contrast, the lane with mother's sample reveal only the two smaller fragments and the absence of the uncut fragment corresponding to the mutant allele. The genetic mutation is further confirmed by subjecting the purified PCR products to automated DNA sequencing (AB1373A; Applied Biosystems, Foster City, Calif.).

V. Corrective Gene Transfer in Ectodermal Dysplasia Using the Human Skin/Inimunodeficient Mouse Xenograft Model.

An amphotropic retroviral vector, with human TAJ expression driven by the retroviral long terminal repeat (LTR), is used to transduce patient keratinocytes in vitro. Following transduction, keratinocytes are grown in 1.5 mM calcium to induce TAJ protein expression. Western blot analysis performed on extracts from control (untranduced) and TAJ-transduced cells demonstrates increased expression of full-length TAJ protein in the transduced cells. BRG1 (Khavari et al. *Nature* 366, 170–174 1993), a constitutively expressed 205-kDa protein, is used as an additional control of cell extract quality, protein concentration and electrophoretic transfer efficiency. This finding demonstrates achievement of effective TAJ gene transfer and expression in ectodermal dysplasia patient-derived keratinocytes. Immunofluorescence staining with TAJ antibody confirms >98% gene transfer efficiency to diseased cells.

Human epidermis are regenerated on immunodeficient mice from keratinocytes grown in vitro; normal as well as transduced and untreated ectodermal dysplasia patient-derived keratinocytes are used. Grafts are clinically well defined and distinct from surrounding mouse skin. The human origin of all tissue utilized is confirmed by using species-specific antibodies to human and mouse epidermal proteins. Expression of differentiation markers for human skin, including basal and suprabasal keratins as well as involucrin, is examined by immunostaining in these grafts and found to be spatially appropriate and consistent with normal human skin.

Clinical hyperkeratosis is seen in a majority of cases in which epidermis is regenerated from untreated keratinocytes from severely afflicted patients. Transduced keratinocytes from the same patients generate skin grafts with less hyperkeratosis and are clinically more similar to epidermis regenerated by keratinocytes from patients with normal skin. These data indicate that TAJ-transduced, regenerated ectodermal dysplasia patient-derived skin displays more normal features of human epidermis, without substantial abnormalities at the levels of clinical appearance, histologic tissue architecture and protein marker expression.

Methods were adapted from Choate et al. (1999) Nature Med 2, 1263–1267. Cells and cell culture. Punch biopsies (6 mm) are taken from patients demonstrating severe hidrotic ectodermal dysplasia (Clouston's syndrome) as well as from control patients with normal skin, under approved institutional protocols for human subjects. Biopsies are stored in SFM (Gibco BRL, Gaithersburg, Md.) with 5 $\mu$g/ml amphotericin and 200 $\mu$g/ml penicillin/streptomycin until culture (Rheinwald & Green. Cell, 6, 331 1975). Each biopsy is bisected, and a portion is used for immunostaining with the remainder placed in 1×sterile dispase with 2.5 $\mu$g/ml amphotricin and 100 $\mu$g/ml penicillin/streptomycin. Biopsies are incubated in dispase solution for 1 h at 37° C. and then placed in sterile PBS where epidemis is removed from the dermis using a sterile forceps and placed into 0.05% trypsin with 2% EDTA for incubation at 37° C. for 20 min with frequent pipetting to release cells. Remaining dermis is scraped at the epidermal interface to release basal keratinocytes. Trypsin is neutralized by DMEM with 10% FCS, then cells are centrifuged at 300 g for 5 min. Cell pellets are resuspended in keratinocyte primary culture medium (DMEM, 10% FCS, 0.05 $\mu$g/ml hydrocortisone, 10 $\mu$g/ml EGF, $10^{-10}$M cholera toxin, 5 $\mu$g/ml insulin, 500 units penicillin/streptomycin and 2.5 $\mu$g/ml amphotericin). The cell resuspension is divided and plated on two 100-mm tissue culture dishes that were preseeded with lethally irradiated 3T3 cells at 30% confluence. Cells are left untouched for 5 days after which they are grown in 50% SFM/50% medium 154 (Cascade Biologics, Portland, Oreg.) with supplements and then used for gene transfer studies.

Retroviral expression vector and gene transfer. The full-length TAJ cDNA (Chaudhary, 1999, WO9911791) is subcloned as an NotI fragment into the LZRS vector, and high-titer retrovirus is prepared in human 293 packaging cells (Kinsella et al. *Hum. Gene Ther.* 7, 1405–1413 1996). Patient cells are dissociated from culture dishes with trypsin-EDTA and counted with a hemocytometer. Cells ($1 \times 10^5$) are plated in each 35-mm well of a six-well cluster plate and incubated 24 h. Before infection, medium is removed, and cells are washed with sterile PBS. SFM/154 (3 ml) with 5 $\mu$g/ml polybrene is added to each well for 5 min and then aspirated from wells before infection. Viral supernatant is diluted to 50% with SFM/154 and supplemented with 5 $\mu$g/ml polybrene. Plates are then centrifuged at 300 g for 1 h at 32° C. They are then placed in a 37° C. incubator for 2 days, after which medium is changed to 3 ml fresh SFM/154.

Western blot analysis. Western blot analysis of TAJ expression is performed using a mouse monoclonal antibody (mAb) to human TAJ. For additional verification, polyclonal rabbit antisera raised to synthetic peptides at the amino- and carboxy-terminal regions of human TAJ are also used. The same blots are incubated simultaneously with a polyclonal antibody to BRG1 (Khavari et al. *Nature* 366, 170–174 1993). BRG1 is a constitutively expressed protein present at comparable amounts in most cell types and serves here as an additional internal control for protein concentration and efficiency of transfer. Approximately 20 $\mu$g of extract protein is loaded per lane.

Immunohistochemistry. Frozen tissue skin sections are fixed and incubated with the mouse mAB to human TAJ, polyclonal antisera to the N and C termini of human TAJ, polyclonal antisera to human involucrin (Murphy et al. *J. Invest. Dermatol.* 82, 453–457 1984), mAb to human filaggrin (Mancini et al. *Pediatr. Res.* 36, 304–314 1994), mAb to human keratin 10 (Ivanyi et al. *J Pathol.* 159, 7–12 1989), or rabbit polyclonal antisera to keratin 14 (Roop et al. *J. Biol. Chem.* 259, 8037–8040 1984). Sections are then washed with PBS/BSA, and treated with anti-mouse peroxidase-conjugated secondary antibody and allowed to react with substrate before analysis.

Regeneration of human epidermis on immunodeficient mice. Primary keratinocytes from patients with severe Clouston syndrome as well as healthy individuals are grown in tissue culture and either left untreated or transduced with optimized retroviral expression vectors for TAJ or β-galactosidase, respectively. Following 48-h infection, cells are given fresh medium and seeded on acellular, devitalized human dermis. After 5 days in tissue culture, grafting to nude or SCID mouse fascia is performed as described (Medalie, et al. *J. Invest. Dermatol.* 107, 121–127 1996).

VI. Localized In Vivo Genotypic and Phenotypic Correction of a TAJ Mutation in a Human Skin/Immunodeficient Mouse Xenograft Model by RNA-DNA Oligonucleotide (RDO).

In this study, we administer a chimeric oligonucleotide multiple times into skin of human skin/immunodeficient mice by topical application and intradermal injection. We demonstrate localized gene correction in vivo by change in skin function, restoration of TAJ activity, and DNA sequence analysis from skin biopsies.

The corrective RDO, hTwt293RDO, is a chimeric oligonucleotide designed to introduce a single base correction in the mutant TAJ gene. It is constructed as described for Tyr-A (Alexeev et al., Nature Biotech, Jan. 2000 18, 43–47) except the tyrosinase sequence is replaced by a wildtype TAJ sequence—TAJ nucleotide 944 flanked by twelve 5' and twelve 3' wildtype TAJ flanking nucleotides (SEQ ID NO: 1, nucleotides 932–956). hTm293RDO is identical to hTwt293RDO except it contains the hTm293 truncating (GGA to TGA) mutation at position 944.

In vivo skin delivery of chimeric oligonucleotide. In vivo application of the chimeric oligonucleotides to mouse skin is carried out by topical application and intradermal injection, as described below. hTM293RDO, which contains an identical sequence to the mutant TAJ, is used as a control.

Cytofectin and fluorescein-isothiocyanate conjugated (FITC) chimeric oligonucleotide complexes are either topically applied or intradermally injected into human skin xenografts growing on immunodeficient mice (See Example V). For topical application, hTwt293RDO or hTm293RDO complexed with Cytofectin is applied daily for three days to the xenograft of four mice. For intradermal injection, the xenografts of four mice are injected with the hTwt293RDO-Cytofectin complex and those of another four mice with hTm293RDO-Cytofectin as a control.

Biopsies are taken 6–8 h after administration, an optimal time for detection of FITC chimeric oligonucleotide, as the fluorescence is significantly defused at later time points (i.e., 18 and 24 h after administration). Fluorescence is generally detected mostly in the hair follicles and epidermis upon topical application. Intradermal injection delivers chimeric oligonucleotide more efficiently, as shown by the higher intensity and uniform distribution of fluorescence among cells in dermis and hair follicles. Fluorescence is not observed in Cytofectin-treated skin.

Gene correction in the treated mice is confirmed at the molecular level using PCR and allele-specific probes in northern and southern blots. For chromosomal PCR analysis, genomic DNA was isolated from skin biopsies from hTwt293RDO- and hTm293RDO-treated mice and subjected to PCR amplification and analysis (see Methods, below). Gene correction in the treated mice is also confirmed by clinical appearance and histologic tissue architecture (see Example V).

Methods were adapted from Alexeev et al., Nature Biotech, Jan. 2000 18, 43–47. In vivo skin delivery of chimeric oligonucleotide. Ten micrograms of FITC-labeled chimeric oligonucleotide are mixed with 10 $\mu$g Cytofectin (Glen Research, Sterling, Va.) in 50 $\mu$l of OptiMEM (Gibco, Bethesda, Md.) for 30 min prior to application. The complexes are topically applied or intradermally injected by 30-gauge needle to human skin xenografts growing on immunodeficient mice prepared as described in Example V. Skin biopsies, 5×5 mm, are taken 6–8 h after injection and transferred to embedding mold filled with O.C.T. compound (Fisher Scientific, Pittsburgh, Pa.). Molds are rapidly submerged into 2-propanol cooled with liquid nitrogen and stored at −80° C. Seven micrometer sections are cut on a microtome (HM 500, Carl Zeiss, Thornwood, N.Y.) at −20° C., and slides analyzed by fluorescence microscopy as described in Alexeev, et al. (1999) Nat. Biotechnol. 16, 1343–1346.

Topical application of chimeric oligonucleotide. The hTwt293RDO and hTm293RDO Cytofectin complexes (15 $\mu$g chimeric oligonucleotide:75 $\mu$g Cytofectin) are prepared in 50 $\mu$l of OptiMEM and applied to the xenografts each day for three days.

Intradermal injections. Mice are injected with 50 $\mu$of hTwt293RDO or hTm293RDO Cytofectin complex (10 $\mu$g chimeric oligonucleotide: 10 $\mu$g Cytofectin) in OptiMEM. Skin biopsies about 10 mm$^2$ were taken from both treated and untreated areas.

Immunostaining and histology. Seven micrometer frozen sections of skin treated with hTwt293RDO or hTm293RDO are made as described above, and subject to immunostaining with an antibody raised against TAJ C-terminal residues 400–420. An average of 100 frozen sections are cut for each specimen from two animals treated with hTwt293RDO and two animals treated with hTwt293RDO. The same slides were stained with hematoxylin-eosin stain (Fisher Scientific) for morphological identification. TAJ expression was also detected using immunostaining (supra) on formalin-fixed paraffin-embedded tissue sections.

PCR amplification, restriction analysis and DNA sequencing. Genomic DNA is isolated with DNAzol (Molecular Research Center, Cincinnati, Ohio) from the skin biopsy samples and amplified by PCR to generate a TAJ gene fragment (forward primer: nucleotides 903–921 of SEQ ID NO: 1; reverse primer: reverse complement of nucleotides 1201–1220 of SEQ ID NO: 1). The purified PCR products are digested with BamHI restriction enzyme, and reaction products analyzed by 12% PAGE. The genetic correction is initially confirmed by appearance of a BamHI site, and further confirmed by subjecting the purified PCR products to automated DNA sequencing (AB1373A; Applied Biosystems, Foster City, Calif.).

To confirm correction at the RNA level, total RNA is isolated from skin biopsy samples by Trizol reagent (Life Technologies). Reverse transcription is performed using random primer and using the Superscript preamplification system for first strand cDNA synthesis (Life Technologies), following the manufacturer's specifications. The resulting cDNA are amplified by PCR suing TAJ specific primers (forward primer: nucleotides 903–921 of SEQ ID NO: 1; reverse primer: reverse complement of nucleotides 1201–1220 of SEQ ID NO: 1). The purified PCR products are digested with BamHI restriction enzyme, and reaction products analyzed by 12% PAGE. The genetic correction is initially confirmed by appearance of a BamHI site, and further confirmed by subjecting the purified PCR products to automated DNA sequencing (AB1373A; Applied Biosystems, Foster City, Calif.).

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting the presence of or predisposition to an ectodermal disorder comprising the steps of:
    (a) detecting the presence of a human TAJ gene or gene product in a cell of a host predetermined to be at elevated risk of having or being predisposed to a particular ectodermal disorder; and
    (b) correlating the presence of the TAJ gene or gene product with a presence of or predisposition to the ectodermal disorder,
    wherein the TAJ gene or gene product is a variant correlated with the presence of or predisposition to the ectodermal disorder,
    wherein the ectodermal disorder is an ectodermal dysplasia syndrome and the syndrome is Clouston syndrome, and
    wherein the detecting step comprises detecting a TAJ gene encoding a truncated TAJ protein mutant of Table 1:

| TAJ Mutant | Genetic Lesion | Translation Product | TAJ Structural Defect |
| --- | --- | --- | --- |
| hTm106 | C deletion at 384 | Ser to Stop at 107 | Truncation at residue 106 |
| hTm134 | T to A at 459 | Cys to Stop at 135 | Truncation at residue 134 |
| hTm174 | C deletion at 589 | Cys to Stop at 175 | Truncation at residue 174 |
| hTm191 | T to A at 639 | Tyr to Stop at 192 | Truncation at residue 191 |
| hTm212 | C to A at 703 | Tyr to Stop at 213 | Truncation at residue 212 |
| hTm219 | T to A at 724 | Cys to Stop at 220 | Truncation at residue 219 |
| hTm238 | CC deletion at 762 | Ala to Val at 233 | Truncation at residue 238 |
| hTm244 | C to A at 799 | Cys to Stop at 245 | Truncation at residue 244 |
| hTm268 | T to A at 871 | Cys to Stop at 269 | Truncation at residue 268 |
| hTm277 | C to T at 896 | Arg to Stop at 278 | Truncation at residue 277 |
| hTm279 | A to T at 902 | Arg to Stop at 280 | Truncation at residue 279 |
| hTm286 | G to T at 923 | Glu to Stop at 287 | Truncation at residue 286 |
| hTm293 | G to T at 944 | Gly to Stop at 294 | Truncation at residue 293. |

2. A method for detecting the presence of or predisposition to an ectodermal disorder comprising the steps of:
    (a) detecting the presence of a human TAJ gene or gene product in a cell of a host predetermined to be at elevated risk of having or being predisposed to a particular ectodermal disorder; and
    (b) correlating the presence of the TAJ gene or gene product with a presence of or predisposition to the ectodermal disorder,
    wherein the TAJ gene or gene product is a variant correlated with the presence of or predisposition to the ectodermal disorder, and
    wherein the detecting step comprises detecting a TAJ gene transcript encoding a truncated TAJ protein mutant of Table 1:

| TAJ Mutant | Genetic Lesion | Translation Product | TAJ Structural Defect |
| --- | --- | --- | --- |
| hTm106 | C deletion at 384 | Ser to Stop at 107 | Truncation at residue 106 |
| hTm134 | T to A at 459 | Cys to Stop at 135 | Truncation at residue 134 |
| hTm174 | C deletion at 589 | Cys to Stop at 175 | Truncation at residue 174 |
| hTm191 | T to A at 639 | Tyr to Stop at 192 | Truncation at residue 191 |
| hTm212 | C to A at 703 | Tyr to Stop at 213 | Truncation at residue 212 |
| hTm219 | T to A at 724 | Cys to Stop at 220 | Truncation at residue 219 |
| hTm238 | CC deletion at 762 | Ala to Val at 233 | Truncation at residue 238 |
| hTm244 | C to A at 799 | Cys to Stop at 245 | Truncation at residue 244 |
| hTm268 | T to A at 871 | Cys to Stop at 269 | Truncation at residue 268 |
| hTm277 | C to T at 896 | Arg to Stop at 278 | Truncation at residue 277 |
| hTm279 | A to T at 902 | Arg to Stop at 280 | Truncation at residue 279 |
| hTm286 | G to T at 923 | Glu to Stop at 287 | Truncation at residue 286 |
| hTm293 | G to T at 944 | Gly to Stop at 294 | Truncation at residue 293. |

3. A method for detecting the presence of or predisposition to an ectodermal disorder comprising the steps of:
    (a) detecting the presence of a human TAJ gene or gene product in a cell of a host predetermined to be at elevated risk of having or being predisposed to a particular ectodermal disorder; and
    (b) correlating the presence of the TAJ gene or gene product with a presence of or predisposition to the ectodermal disorder,
    wherein the TAJ gene or gene product is a variant correlated with the presence of or predisposition to the ectodermal disorder, and
    wherein the detecting step comprises detecting a truncated TAJ protein mutant of Table 1:

| TAJ Mutant | Genetic Lesion | Translation Product | TAJ Structural Defect |
| --- | --- | --- | --- |
| hTm106 | C deletion at 384 | Ser to Stop at 107 | Truncation at residue 106 |
| hTm134 | T to A at 459 | Cys to Stop at 135 | Truncation at residue 134 |
| hTm174 | C deletion at 589 | Cys to Stop at 175 | Truncation at residue 174 |
| hTm191 | T to A at 639 | Tyr to Stop at 192 | Truncation at residue 191 |
| hTm212 | C to A at 703 | Tyr to Stop at 213 | Truncation at residue 212 |
| hTm219 | T to A at 724 | Cys to Stop at 220 | Truncation at residue 219 |
| hTm238 | CC deletion at 762 | Ala to Val at 233 | Truncation at residue 238 |
| hTm244 | C to A at 799 | Cys to Stop at 245 | Truncation at residue 244 |
| hTm268 | T to A at 871 | Cys to Stop at 269 | Truncation at residue 268 |
| hTm277 | C to T at 896 | Arg to Stop at 278 | Truncation at residue 277 |
| hTm279 | A to T at 902 | Arg to Stop at 280 | Truncation at residue 279 |
| hTm286 | G to T at 923 | Glu to Stop at 287 | Truncation at residue 286 |
| hTm293 | G to T at 944 | Gly to Stop at 294 | Truncation at residue 293. |

* * * * *